United States Patent [19]

Levin et al.

[11] 4,121,453
[45] Oct. 24, 1978

[54] FOOT FORCE TRANSDUCER

[75] Inventors: Richard C. Levin, Pasadena; Allan G. Armstrong, Santa Rosa, both of Calif.

[73] Assignee: Harvey Mudd College, Claremont, Calif.

[21] Appl. No.: 706,487

[22] Filed: Jul. 19, 1976

[51] Int. Cl.$^2$ .............................................. A61B 5/00
[52] U.S. Cl. ..................................................... 73/172
[58] Field of Search ............. 73/172, 141 A, 88.5 SD, 73/88.5 R; 338/2, 3, 5, 6

[56] References Cited

U.S. PATENT DOCUMENTS

| 3,151,480 | 10/1964 | Schultz | 73/141 A |
| 3,451,030 | 6/1969 | Garfinkel | 73/88.5 SD |
| 3,456,226 | 7/1969 | Vick | 73/88.5 SD |
| 3,913,392 | 10/1975 | Nagase et al. | 73/88.5 SD |
| 3,967,188 | 6/1976 | Spencer | 73/88.5 R |

Primary Examiner—Donald O. Woodiel
Attorney, Agent, or Firm—Lyon & Lyon

[57] ABSTRACT

An apparatus for measuring foot forces during walking uses a specially configured spring seated in a transducer plate to transmit static and dynamic forces on the foot during walking to strain gauges mounted on the transducer plate, which, in turn, may be monitored and recorded for diagnostic purposes, particularly to aid in treating patients with lower extremity dysfunction.

12 Claims, 4 Drawing Figures

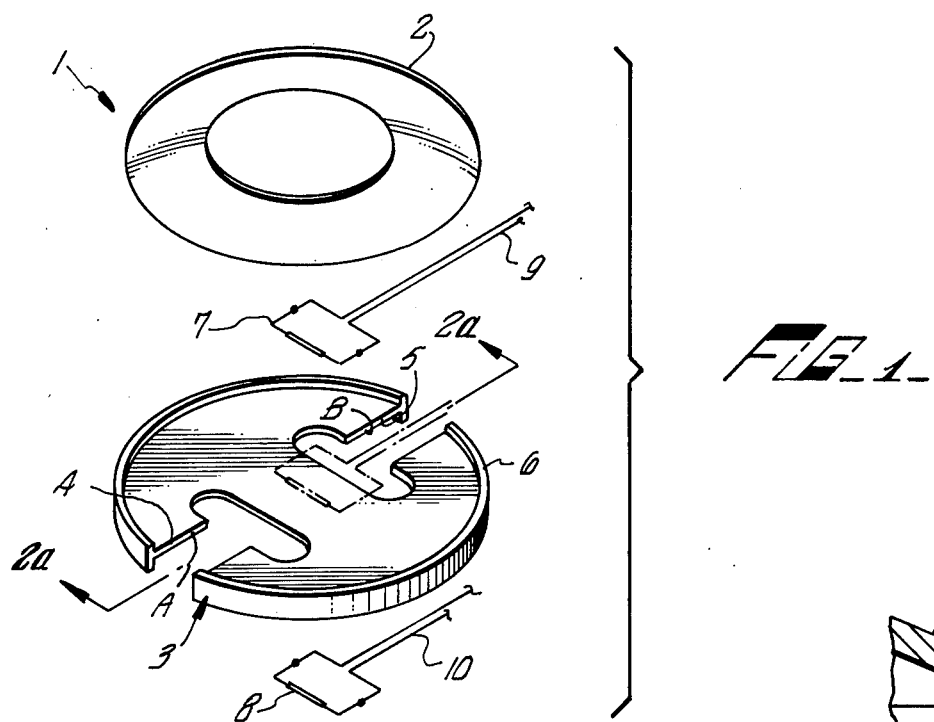
FIG_1_
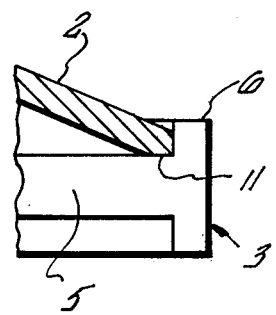
FIG_2b_
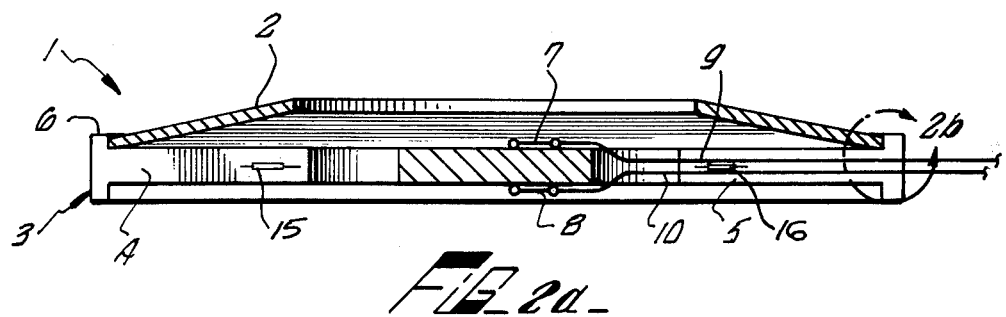
FIG_2a_
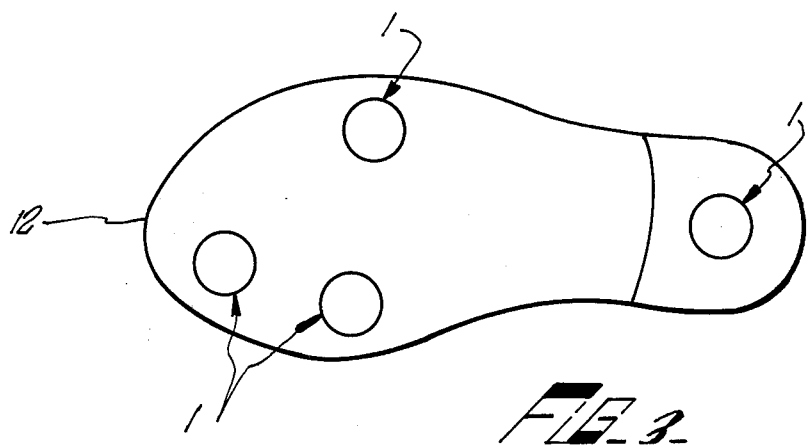
FIG_3_

FOOT FORCE TRANSDUCER

BACKGROUND OF THE INVENTION

The present invention was developed by the present inventors as part of a project by the Engineering Clinic of Harvey Mudd College for Rancho Los Amigos Hospital for aid in the treatment of patients with abnormal gait due to lower extremity malfunction. The analysis of foot forces helps in locating the cause and severity of the disability and to help in evaluating past treatment, either surgical or therapeutic, as well as providing information for future treatment.

The most commonly used system in the prior art has been a force-sensitive plate imbedded in a walking surface. However, such plates typically are suitable only for measuring the total forces over the entire foot occurring during a single step, and require the patient to walk over the plate several times to obtain a sufficient data base. Such a time consuming and repetitive procedure may be so painful to some patients as to be intolerable. Further, while such plates enable accurate data to be obtained, since they typically employ piezoletric sensors and charge amplifiers, the sensors tend both to limit plate size and make cost prohibitive. Additionally, since such plates sense only total foot forces, it is impossible to determine the areas of the foot where the forces are being exerted.

Photographic techniques have also been used in documenting defects in gait, but such techniques tend to involve considerable expense. A third method, that of placing microswitches in various positions in the insole of the patient's shoe, permits forces at any position on the foot to be sensed, but gives only a position indication and not an indication of the magnitude of the forces.

An earlier, less successful transducer developed in 1974 by others at the Engineering Clinic of Harvey Mudd College employed a configuration similar to the present invention, although different in several important respects. The earlier configuration used a slotted transducer plate as with the present invention, a single strain gauge and two Belleville springs, rather than a single spring and two strain gauges as in the present invention. The single strain gauge was positioned on the transducer plate between the two slots and perpendicular thereto and, similar to that described hereinafter for the present invention, the two Belleville springs were fitted into a retaining lip on either side of the transducer plate. Thus a force applied to the transducer created primarily an axial strain in the transducer plate since any bending moment was minimized by the use of a Belleville spring on either side of the transducer plate. In constrast and as will be described in detail hereinafter, the present invention operates by monitoring the bending moment in the transducer plate. In addition, the previous transducer suffered from poor linearity of response and exhibited rather high hysteresis, whereas the present invention maintains good linearity and substantially reduced hysteresis.

Thus the need has existed for an accurate transducer small enough to permit placing several such transducers on a single shoe, but which indicates the magnitude of a force, without significantly interfering with the patient's gait.

SUMMARY OF THE INVENTION

The present invention provides a transducer small enough to permit placing one transducer in at least four areas of the sole of a shoe or sandal; namely, the heel, the first metatarsal, the fifth metatarsal and the great toe. The transducer typically is approximately 0.159 inches thick (unloaded) and so does not interfere significantly with a patient's normal gait when the transducers are imbedded in a sole suitable for being strapped onto a patient's shoes. It is desirable that the transducers be imbedded in a strap-on or otherwise detachable device since many patients who would benefit from the present invention walk only with special shoes and/or leg braces.

In one embodiment, the transducer of the present invention uses a Belleville spring mounted in a relatively rigid plate of metal or other suitable material. Strain gauges are attached to the plate so that when the Belleville spring is compressed as a result of of a foot force, the stress causes the transducer plate to flex, and the resistances of the strain gauges affixed to the transducer plate vary with the flexing of the plate. A sensing circuit may then be used to generate a signal responsive to variations in the strain gauge resistance. Various means, such as telemetry devices or cables, may be used to communicate the signals generated by the strain gauges and associated sensing circuitry to data recording equipment. However, since reproduction of the patient's normal gait during diagnosis is highly desirable, devices such as telemetry systems which do not significantly encumber the patient while walking are preferable.

An object of this invention is to provide a new form of force transducer. An additional object of this invention is to provide a foot force transducer adapted to be implanted in the sole of a shoe suitable for accurately indicating the magnitude of the foot forces generated during normal walking.

Another object of the present invention is to provide a system for accurately monitoring the foot forces generated at a plurality of locations on the foot during normal walking.

Other and further objects of the present invention will become apparent in the course of the following detailed description.

THE DRAWINGS

FIG. 1 diagrammatically illustrates an exploded perspective view of the transducer of the present invention.

FIG. 2a diagrammatically illustrates a cross-sectional side view of the transducer of the present invention.

FIG. 2b illustrates an enlarged portion of the cross-sectional view of the transducer.

FIG. 3 diagrammatically illustrates a bottom view of a strap-on sole of a shoe into which a plurality of the transducers shown in FIGS. 1a–1b have been implanted.

DESCRIPTION OF THE PREFERRED EMBODIMENTS

Referring to FIG. 1, which illustrates an exploded view of a preferred embodiment of the present invention, the transducer 1 is comprised of spring 2 fitted snugly into a transducer plate 3. The spring 2 is typically a Belleville spring, but any arcuate toroidal spring is acceptable. The transducer plate 3 is typically constructed in a circular shape of stainless steel, although any similarly rigid material will do, with two slots 4 and 5 aligned along a diameter of the plate 3. The outer edge of the plate 3 provides a lip 6 into which the spring 2 may be fitted. Mounted on the plate 3 perpendicular to and bisected by the axis of the slots 4 and 5 in the plate 3 are two strain gauges 7 and 8. One strain gauge 7 is attached to the upper surface of the plate 3, as shown in phantom in FIG. 1, and the remaining strain gauge 8 is attached to the lower surface thereof parallel to gauge 7 in a manner to be described subsequently. The lip 6 extends below the plate 3 to protect the strain gauge 8. The wire leads 9 and 10 from the strain gauges 7 and 8, respectively, are then fed through one of the slots 7 and 8 in the plate 3 to amplifier and monitoring circuitry (not shown). The wire leads may be protected at the transducer by being fed through a flexible insulating tube (not shown) which may be glued onto the transducer plate 3.

The operation of the transducer 1 may be more clearly understood by reference to FIG. 2a, which illustrates a cross-sectional side view of the assembled transducer 1. With reference to FIG. 2a, when a force such as that which occurs during walking, is applied vertically to the spring 2, the spring 2 transmits a force with radial and vertical components to the lip of plate 3. Since the radial component is applied above the neutral plane of the plate, that component creates a bending stress which tends to bow the plate upward as seen in FIG. 2b namely in the direction of curvature of the spring 2. The curvature of the spring 2, convex away from the plate 3, is particularly illustrated in FIG. 2a. In addition, the radial component also creates an axial load through the retaining lip on the transducer plate 3.

The vertical component of the force is transmitted through the lip to the surface supporting the transducer 1, creating a bending moment which tends to bend the plate 3 downward, or away from the direction of curvature of the spring 2. It has been determined that so long as the spring 2 is not completely flat, the radial component dominates the vertical component such that the plate 3 bends upward, or in the same direction as the curvature of the spring 2 as shown in FIG. 2a. Preferably, the spring 2 will not become completely flat below approximately 400 pounds, although the actual value for the spring 2 may be varied depending upon the weight range of the patients whose gait will be diagnosed with the transducer.

It especially should be recognized that the movement of this spring 2 is constrained somewhat by the lip 6 of the plate 3, into which the spring 2 fits. Thus, for example, a spring 2 which may be flat with the application of 285 pounds of force in an unconstrained design may not be flattened until the application of approximately 400 pounds of force in the application shown herein where the movement of the spring 2 is constrained by the plate 3.

As the plate 3 flexes under the stresses caused by the vertical force applied to the spring 2 during walking, the strain gauges 7 and 8 change their resistance in response to the flexing of the plate 3. In particular, the upper strain gauge 7 responds to the sum of the axial strain plus the upward bending strain of the plate 3 while the lower strain gauge 8 responds to the axial strain minus the upward bending strain. By connecting the strain gauges 7 and 8 in opposite legs of a Wheatstone bridge configuration, the signals generated by bending strain cancel out leaving a signal proportional to only the axial strain. The cancellation occurs because the bending strain detected by the stretching of the upper strain gauge 7 will be equal in magnitude to the compression of the lower strain gauge 8, while the same axial strain component is present in both gauges 7 and 8. The other legs of the Wheatstone bridge use known resistances, with one of the resistances being variable so as to zero the bridge in a conventional manner. This configuration is preferable since it provides the most linear response of output voltage to force. Alternatively, the bending strain component may be measured, and the axial strain component cancelled out, by connecting the gauges 7 and 8 in adjacent legs of the bridge.

The transducer 1 must be carefully manufactured to minimize hysteresis as well as maintain good linearity of the strain gauge signal. Hysteresis is primarily a function of friction between the plate 3 and the spring 2. To reduce hysteresis, therefore, a lubricant may be used between the spring 2 and the plate 3 at the junction therebetween as shown in FIG. 2b, which shows in enlarged detail the junction between the spring 2 and the transducer plate 3. However, it has been discovered that lubricants have no long-term effect. A better method of reducing hysteresis is to polish or slightly flatten the bottom edge 11 of the spring 2 at the point where it contacts plate 3 as shown in FIG. 2b. Fine emery paper on a flat surface is suitable for polishing the bottom edge 11 of the spring 2. Polishing permits the edge 11 of the spring 2 to slide more smoothly over the plate 3 than an unpolished spring. Further, hysteresis is reduced additionally by a break-in period of approximately 1,000 cycles between approximately 20 and 250 pounds of force.

To increase the linearity of the response of the transducer 1, the previously mentioned slots 4 and 5 are milled in plate 3 to permit a more predictable flexing of the transducer 1. However, these slots could be eliminated without considerable adverse effect on the operation of the transducer 1 merely by using only the top strain gauge 7 and eliminating the bottom strain guage 8. Some loss in sensitivity may result from this alternative configuration. In addition to providing the slots 4 and 5 in plate 3, linearity is increased by ensuring that the spring 2 fits very tightly into plate 3. Unless the spring 2 is fitted tightly into the plate 3, a "dead zone" results at low forces. This is because the spring 2 may flatten somewhat without causing a bending moment in the plate 3 unless the outer diameter of the spring 2 is extremely close to the inner diameter of the lip on the plate 3. In fitting the spring 2 to the plate 3, for proper operation at least a 10 ohm increase should be seen in the top gauge 7 (described below) and a corresponding drop of at least 3 ohms should be seen in the bottom gauge 8 when the transducer 1 is unloaded. By ensuring a relatively tight fit of the spring 2 into the plate 3, and polishing the bottom surface on spring 2 as described above, good linearity with minimal hysteresis results.

Strain gauges 7 and 8 are preferably matched semiconductor gauges with a gauge factor of approximately 140, compared to the gauge factor of five associated with foil type gauges. Those skilled in the art will recognize that gauge factor is the ratio of resistance change to incremental strain. The strain gauges 7 and 8 are secured to the plate 3 typically by an epoxy, and a synthetic rubber compound may be applied after mounting to protect the gauges, leads and solder tabs from damage which can occur through negligent touching or other contact with the gauges 7 and 8 on the plate 3.

It should be noted that the strain gauges 7 and 8, being comprised of semiconductor material, are subject to temperature drift. Temperature compensation may be provided by substituting matched strain gauges for the remaining two legs of the Wheatstone bridge with an additional variable resistor to permit zeroing the bridge. However, the additional matched strain gauges increase the expense of the transducer 1 and create some error due to DC offset. Should temperature compensation be desired, the additional strain gauges 15 and 16 (FIG. 2a) should be mounted horizontally on the edge of the milled slots in plate 3, where they will not be subject to either the vertical or the axial strain caused by a force on the transducer, as at points A and B shown in FIG. 1.

Considering FIG. 3, which illustrates a plurality of the transducers 1 in the sole 12 of a sandal or shoe, it becomes apparent how the transducer 1 described above provides an indication of the order and magnitude of various forces on a patient's foot during walking. Preferably, the sole 12 is simply a slip-on sandal which may be worn over the patient's shoe since many of the patients who will benefit from the transducer 1 described herein are required to wear special shoes or braces. During diagnosis, two such sandals are used, one for each foot. Thus, the sole 12 typically has buckle straps (not shown) to hold the sole 12 onto a respective one of the patient's shoes.

With this in mind, it is apparent that the sole 12 or sandal must be thin enough and of such a construction as to not interfere with the patient's "normal" gait. Also, the sandal or sole 12 must not slip during walking and should be adjustable so that a single pair of sandals may be worn by a number of different patients for diagnostic purposes. Further, the sandals must permit the spring 2 of the transducer 1 to protrude slightly from the sole 12 so as to touch the walking surface and thereby receive the forces on the foot during walking.

To accomplish the above objectives, the sandal 12 is constructed of two pieces with separate heel and half-sole sections so that some size adjustments are possible. Typically, a ⅛ inch thick sheet of Shore 80 rubber or other hard rubber is attached to a leather sheet of 7 to 8 ounce shoulder hide. Four holes of sufficient size to permit placement therein of the transducers 1 are made in the rubber sheet so as to permit the transducers 1 to protrude slightly during walking. Between the transducers 1, on the side on which strain gauge 8 is located, and the leather backing sheet are typically placed discs of plastic or other material to prevent the leather of the sole 12 from contacting the strain gauge 8. To protect the transducers 1 during contact with the floor, the transducers 1 are preferably covered with a thin, flexible material such as fabric tape (not shown) or some similar substance. The tape or other material may have to be replaced after repeated use due to wearing.

The thickness of the leather backing may be varied substantially without significant adverse effect on the general operation of the transducer system. However, the thermal drift of the semiconductor strain gauges 7 and 8 noted above typically increases with decreasing thickness of the leather sole, so a thicker but still flexible sole may be preferable to minimize thermal drift. In order to prevent the sandal from slipping on the patient's shoe, buckle straps are included and a bracket of metal or other rigid material (not shown) may be installed at the heel so the heel piece cannot slide forward on the foot.

The strain gauge leads from each of the four transducers 1 in the sandal may be connected by tubing in grooves cut into the bottom face of the rubber sheet. Preferably, all leads from the transducers are terminated at a single connector for each sandal. The connector may be fastened to the sandal 12 with a leather or sheet metal encasement which may be riveted to one of the fastening straps. The connector is used to connect strain gauges 7 and 8 to the monitoring and telemetry circuitry described hereinafter. The heel and half-sole sections of the sandal 12 are typically connected by a flexible strap of tape or other material. Depending upon the placement of the connector, this strap of material will contain the transducer leads from either the half-sole or the heel transducers 1.

As will be apparent to those familiar with the art, the signal supplied at the output of the Wheatstone bridge, which includes the strain gauges, must be amplified in order to be usable, such as being recorded on a strip chart recorder or other device. A high-gain, low-noise operational amplifier such as a National Semiconductor LM 324 module provides a suitable operational amplifier for purposes of the present invention. The amplifier may be comprised of multiple stages of operational amplifiers with a first stage configured as a voltage follower to present a high load impedance to the bridges, and subsequent stages configured to provide a total amplification variable from less than 20 to well over 100. By providing such an amplifier circuit, it is possible to provide ten millivolts output per pound of applied force for any variation in transducer behavior likely to occur during loading by a patient's walking. The output of the amplifier stages may then be either summed with the amplified signals from the other transducers or may be monitored individually; in either configuration, the amplified transducer output is fed into a data recording means, such as a strip chart recorder or other recording device.

Preferably, the amplifier and summing stages are carried on the patient, and so must be operated at a low voltage so as not to endanger the person if an electrical fault should occur. Thus, for example, the system may be operated on ±5 volts supplied by two 9.6 volt batteries and a regulated supply. If desired, a voltage sensing circuit with a light emitting diode may be supplied to indicate that the voltage of the batteries has fallen to an insufficient level.

Because the amplifier stages may be comprised of integrated operational amplifiers, there should be no difficulty in constructing the amplifier circuitry in such a manner as to be portably mounted on a patient, either at the waist or elsewhere. Naturally, a connecting cable will be required between the sandals (at the above-described connector) and amplifier stages. These signals may be communicated to the data recording means either by telemetry equipment worn by the patient or through cables attached to the amplifier stages and carried by the patient as he walks. Preferably, telemetry equipment is used since it increases the mobility of the patient and, hence, more accurately reproduces the patient's natural gait. Those skilled in the art will recognize from the detailed description herein numerous equivalents which do not depart from the present invention and are to be understood as included herein.

We claim:

1. A transducer for measuring the magnitude of an applied force comprising an arcuate toroidal spring which flattens a predetermined amount in proportion to the magnitude of an applied force, a circular plate of relatively rigid material having a circumferential lip of a diameter substantially equal to the outer diameter of said spring such that the flattening of said spring upon application of a force causes said plate to flex, that portion of the lower surface of said spring which contacts said plate being polished to reduce hysteresis, and strain sensing means for indicating the magnitude of flexing of said circular plate.

2. A transducer as in claim 1 wherein said arcuate toroidal spring is a Belleville spring.

3. A transducer as in claim 2 wherein said strain sensing means comprises at least one strain gauge.

4. A transducer as in claim 2 wherein said strain sensing means comprises two semiconductor strain gauges, one mounted on the upper side of said plate and the second mounted parallel to said first gauge on the underside of said plate.

5. A transducer as in claim 1 wherein said circular plate has slots along a diameter and said strain sensing means is a pair of strain gauges symmetrically disposed perpendicular to said diameter, one on the upper side of said plate and the second on the lower side of said plate.

6. A transducer for indicating the magnitude of an applied force comprising a flat circular plate of relatively rigid material having a circumferential lip and a pair of symmetric slots extending inwardly along a diameter, a Belleville spring having an outer diameter substantially equal to the inner diameter of the circumferential lip and mounted within the circumferential lip of said plate such that the flattening of the Belleville spring upon appplication of a force causes said plate to flex in response to the applied force, and a pair of semiconductor strain gauges, the first mounted on the upper side of said plate between and perpendicular to said symmetric slots and the second mounted on the lower side of said plate between and perpendicular to said slots, said semiconductor strain gauges being interconnected to provide an output signal representative of only the axial component of the flexing of said plate.

7. A device for measuring foot forces during walking and having a plurality of transducers mounted at predetermined locations iwthin the sole of a sandal adapted to be worn by a patient, each transducer having a Belleville spring tightly fitted within a circumferential lip of a relatively rigid flat circular plate and strain gauge means for sensing a flexing of said plate upon application of a force to said spring.

8. A transducer for measuring the magnitude of an applied force comprising an arcuate toroidal spring which flattens a predetermined amount in proportion to the magnitude of an applied force, a circular plate of relatively rigid material having a circumferential lip of a diameter substantially equal to the outer diameter of said spring such that the flattening of said spring upon application of a force causes said plate to flex, strain sensing means for indicating the magnitude of flexing of said circular plate, wherein said circular plate has slots along a diameter and said strain sensing means is a pair of strain gauges symmetrically disposed perpendicular to said diameter, one on the upper said of said plate and the second on the lower side of said plate, and a second pair of strain gauges adapted for connection to said strain sensing means for compensating for variations in ambient temperature.

9. A transducer for measuring the magnitude of an applied force comprising an arcuate toroidal spring which flattens a predetermined amount in proportion to the magnitude of an applied force, a circular plate of relatively rigid material having a circumferential lip of a diameter substantially equal to the outer diameter of said spring such that the flattening of said spring upon application of a force causes said plate to flex, wherein said circular plate has a pair of slots along a diameter, each of said slots having an edge, a first protion of said edge being substantially devoid of strees during loading, and a second portion of said edge being substantially stressed during loading, strain sensing means for indicating the magnitude of flexing of said circular plate, wherein said strain sensing means is a pair of strain gauges symmetrically disposed perpendicular to said diameter, one on the upper side of said plate and the second on the lower side of said plate, and means adopted for connection to said strain sensing means for connecting for variations in ambient temperature, wherein said temperature compensating means comprises an additional pair of strain gauges, said first additional strain gauge being horizontally affixed to the first portion of said edge of said first slot, and said second additional strain gauge being horizontally affixed to the first protion of said edge of said second slot.

10. A transducer for measuring the magnitude of an applied force comprising an arcuate toroidal spring having an outer diameter which flattens a predetermined amount in porportion to an applied force, a plate having a substantially circular lip having an inner diameter and having a pair of slots extending inwardly along a diameter, such that the flattening of said spring upon application of a force causes said plate to flex, strain sensing means affixed to said plate for sensing the magnitude of flexing of said plate, said outer diameter having a magnitude extremely close to said inner diameter to cause said strain sensing means to sense a predetermined flexing of said plate when no force is applied to said spring.

11. A force transducer comprising an arcuate toroidal spring which flattens a predetermined amount in proportion to the magnitude of an applied force, a substantially circular plate of relatively rigid material having a substantially circumferential lip substantially equal to the outer diameter of said spring such that the flattening of said spring upon application of a force causes said plate to flex, said flexing having an axial component and a bending component, a first pair of strain gauges affixed to said plate and configured to provide a signal representative of said axial component of said flexing.

12. A force transducer as in claim 11 further including a second pair of strain gauges affixed to said plate in a position subject to substantially no stress when a force is applied to said spring, said first and second pairs of strain gauges being interconnected in a Wheatstone bridge configuration such that said second pair of strain gauges compensates for variations in ambient temperature.

* * * * *